(12) United States Patent
Nicholas

(10) Patent No.: US 11,864,763 B2
(45) Date of Patent: Jan. 9, 2024

(54) ADAPTER ASSEMBLY WITH PULLEY SYSTEM AND WORM GEAR DRIVE FOR INTERCONNECTING ELECTROMECHANICAL SURGICAL DEVICES AND SURGICAL END EFFECTORS

(71) Applicant: Covidien LP, Mansfield, MA (US)

(72) Inventor: David Nicholas, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/987,990

(22) Filed: Nov. 16, 2022

(65) Prior Publication Data
US 2023/0072521 A1 Mar. 9, 2023

Related U.S. Application Data

(63) Continuation of application No. 17/034,490, filed on Sep. 28, 2020, now Pat. No. 11,504,123, which is a
(Continued)

(51) Int. Cl.
*A61B 17/072* (2006.01)
*A61B 34/00* (2016.01)
(Continued)

(52) U.S. Cl.
CPC ........ *A61B 17/07207* (2013.01); *A61B 34/71* (2016.02); *A61B 2017/0046* (2013.01);
(Continued)

(58) Field of Classification Search
CPC .............. A61B 17/07207; A61B 34/71; A61B 2034/715; A61B 2017/00398;
(Continued)

(56) References Cited

U.S. PATENT DOCUMENTS 2,777,340 A   1/1957  Hettwer et al.
2,957,353 A   10/1960 Babacz
(Continued)

FOREIGN PATENT DOCUMENTS

CA   2451558 A1   1/2003
CA   2824590 A1   4/2014
(Continued)

OTHER PUBLICATIONS

Chinese Office Action for application No. 2021111861697 with English Translation.
(Continued)

*Primary Examiner* — Dariush Seif
(74) *Attorney, Agent, or Firm* — Carter, DeLuca & Farrell LLP

(57) ABSTRACT

An adapter assembly for selective connection to a surgical device is provided. The adapter assembly includes an outer tube having a distal end and a proximal end, a housing secured to the proximal end of the outer tube, and a cable drive assembly supported by the housing. The cable drive assembly includes a worm gear drive assembly, a cable gear assembly coupled to the worm gear drive assembly, and one or more cables coupled to the cable gear assembly and axially translatable within the outer tube.

20 Claims, 11 Drawing Sheets

Related U.S. Application Data continuation of application No. 15/491,268, filed on Apr. 19, 2017, now Pat. No. 10,799,239.

(60) Provisional application No. 62/333,584, filed on May 9, 2016.

(51) Int. Cl.
  *A61B 17/00* (2006.01)
  *A61B 17/29* (2006.01)

(52) U.S. Cl.
  CPC ........... *A61B 2017/00398* (2013.01); *A61B 2017/00473* (2013.01); *A61B 2017/07285* (2013.01); *A61B 2017/2927* (2013.01); *A61B 2034/715* (2016.02)

(58) Field of Classification Search
  CPC .. A61B 2017/0046; A61B 2017/00473; A61B 2017/07285; A61B 2017/2927
  USPC ...... 227/175.1–182.1; 606/75, 151, 219, 220
  See application file for complete search history.

(56) References Cited

U.S. PATENT DOCUMENTS

| | | | |
|---|---|---|---|
| 3,006,885 A | 10/1961 | Marczyk | |
| 3,025,199 A | 3/1962 | Whitman et al. | |
| 3,111,328 A | 11/1963 | Di Rito et al. | |
| 3,695,058 A | 10/1972 | Keith, Jr. | |
| 3,734,515 A | 5/1973 | Dudek | |
| 3,759,336 A | 9/1973 | Marcovitz et al. | |
| 4,162,399 A | 7/1979 | Hudson | |
| 4,544,090 A * | 10/1985 | Warman | B25C 1/06 |
| | | | 227/134 |
| 4,606,343 A | 8/1986 | Conta et al. | |
| 4,705,038 A | 11/1987 | Sjostrom et al. | |
| 4,722,685 A | 2/1988 | de Estrada et al. | |
| 4,823,807 A | 4/1989 | Russell et al. | |
| 4,874,181 A | 10/1989 | Hsu | |
| 5,129,118 A | 7/1992 | Walmesley | |
| 5,129,570 A | 7/1992 | Schulze et al. | |
| 5,152,744 A | 10/1992 | Krause et al. | |
| 5,301,061 A | 4/1994 | Nakada et al. | |
| 5,312,023 A * | 5/1994 | Green | A61B 17/07207 |
| | | | 227/19 |
| 5,326,013 A | 7/1994 | Green et al. | |
| 5,350,355 A | 9/1994 | Sklar | |
| 5,383,874 A | 1/1995 | Jackson et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,400,267 A | 3/1995 | Denen et al. | |
| 5,411,508 A | 5/1995 | Bessler et al. | |
| 5,413,267 A | 5/1995 | Solyntjes et al. | |
| 5,427,087 A | 6/1995 | Ito et al. | |
| 5,433,721 A | 7/1995 | Hooven et al. | |
| 5,467,911 A * | 11/1995 | Tsuruta | A61B 17/0684 |
| | | | 227/19 |
| 5,476,379 A | 12/1995 | Disel | |
| 5,487,499 A | 1/1996 | Sorrentino et al. | |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,540,375 A | 7/1996 | Bolanos et al. | |
| 5,540,706 A | 7/1996 | Aust et al. | |
| 5,542,594 A | 8/1996 | McKean et al. | |
| 5,549,637 A | 8/1996 | Crainich | |
| 5,553,675 A | 9/1996 | Pitzen et al. | |
| 5,562,239 A | 10/1996 | Boiarski et al. | |
| 5,564,615 A | 10/1996 | Bishop et al. | |
| 5,582,617 A * | 12/1996 | Klieman | A61B 34/71 |
| | | | 606/174 |
| 5,609,560 A | 3/1997 | Ichikawa et al. | |
| 5,626,587 A | 5/1997 | Bishop et al. | |
| 5,632,432 A | 5/1997 | Schulze et al. | |
| 5,645,209 A | 7/1997 | Green et al. | |
| 5,647,526 A | 7/1997 | Green et al. | |
| 5,653,374 A | 8/1997 | Young et al. | |
| 5,658,300 A | 8/1997 | Bito et al. | |
| 5,662,662 A | 9/1997 | Bishop et al. | |
| 5,667,517 A | 9/1997 | Hooven | |
| 5,693,042 A | 12/1997 | Boiarski et al. | |
| 5,704,534 A | 1/1998 | Huitema et al. | |
| 5,711,472 A * | 1/1998 | Bryan | A61B 17/07207 |
| | | | 227/19 |
| 5,713,505 A | 2/1998 | Huitema | |
| 5,762,603 A | 6/1998 | Thompson | |
| 5,779,130 A | 7/1998 | Alesi et al. | |
| 5,782,396 A | 7/1998 | Mastri et al. | |
| 5,782,397 A | 7/1998 | Koukline | |
| 5,792,135 A * | 8/1998 | Madhani | A61B 34/77 |
| | | | 606/1 |
| 5,792,573 A | 8/1998 | Pitzen et al. | |
| 5,797,536 A | 8/1998 | Smith et al. | |
| 5,820,009 A | 10/1998 | Melling et al. | |
| 5,863,159 A | 1/1999 | Asko | |
| 5,908,427 A | 6/1999 | McKean et al. | |
| 5,954,259 A | 9/1999 | Viola et al. | |
| 5,964,774 A | 10/1999 | McKean et al. | |
| 5,993,454 A | 11/1999 | Longo | |
| 6,010,054 A | 1/2000 | Johnson et al. | |
| 6,017,354 A | 1/2000 | Culp et al. | |
| 6,032,849 A | 3/2000 | Mastri et al. | |
| 6,045,560 A | 4/2000 | McKean et al. | |
| 6,080,185 A * | 6/2000 | Johnson | A61B 17/8872 |
| | | | 606/103 |
| 6,090,123 A | 7/2000 | Culp et al. | |
| 6,126,651 A | 10/2000 | Mayer | |
| 6,129,547 A | 10/2000 | Cise et al. | |
| 6,165,169 A | 12/2000 | Panescu et al. | |
| 6,239,732 B1 | 5/2001 | Cusey | |
| 6,241,139 B1 | 6/2001 | Milliman et al. | |
| 6,250,532 B1 * | 6/2001 | Green | A61B 17/07207 |
| | | | 227/19 |
| 6,264,086 B1 | 7/2001 | McGuckin, Jr. | |
| 6,264,087 B1 | 7/2001 | Whitman | |
| 6,302,311 B1 | 10/2001 | Adams et al. | |
| 6,315,184 B1 | 11/2001 | Whitman | |
| 6,321,855 B1 | 11/2001 | Barnes | |
| 6,329,778 B1 | 12/2001 | Culp et al. | |
| 6,343,731 B1 | 2/2002 | Adams et al. | |
| 6,348,061 B1 | 2/2002 | Whitman | |
| 6,368,324 B1 | 4/2002 | Dinger et al. | |
| 6,371,909 B1 | 4/2002 | Hoeg et al. | |
| 6,434,507 B1 | 8/2002 | Clayton et al. | |
| 6,443,973 B1 | 9/2002 | Whitman | |
| 6,461,372 B1 | 10/2002 | Jensen et al. | |
| 6,488,197 B1 | 12/2002 | Whitman | |
| 6,491,201 B1 | 12/2002 | Whitman | |
| 6,533,157 B1 | 3/2003 | Whitman | |
| 6,537,280 B2 | 3/2003 | Dinger et al. | |
| 6,610,066 B2 | 8/2003 | Dinger et al. | |
| 6,611,793 B1 | 8/2003 | Burnside et al. | |
| 6,645,218 B1 | 11/2003 | Cassidy et al. | |
| 6,654,999 B2 | 12/2003 | Stoddard et al. | |
| 6,698,643 B2 | 3/2004 | Whitman | |
| 6,699,177 B1 | 3/2004 | Wang et al. | |
| 6,716,233 B1 | 4/2004 | Whitman | |
| 6,743,240 B2 | 6/2004 | Smith et al. | |
| 6,783,533 B2 | 8/2004 | Green et al. | |
| 6,792,390 B1 | 9/2004 | Burnside et al. | |
| 6,793,652 B1 | 9/2004 | Whitman et al. | |
| 6,817,508 B1 | 11/2004 | Racenet et al. | |
| 6,830,174 B2 | 12/2004 | Hillstead et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,860,892 B1 | 3/2005 | Tanaka et al. | |
| 6,899,538 B2 | 5/2005 | Matoba | |

(56) References Cited

U.S. PATENT DOCUMENTS

| | | | |
|---|---|---|---|
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,006,885 B2 * | 8/2011 | Marczyk ......... A61B 17/07207 227/176.1 |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,556,152 B2 | 10/2013 | Marczyk et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |

(56) References Cited

U.S. PATENT DOCUMENTS

| | | | |
|---|---|---|---|
| 8,931,680 B2 | 1/2015 | Milliman | |
| 8,939,344 B2 | 1/2015 | Olson et al. | |
| 8,950,646 B2 | 2/2015 | Viola | |
| 8,960,519 B2 | 2/2015 | Whitman et al. | |
| 8,961,396 B2 | 2/2015 | Azarbarzin et al. | |
| 8,967,443 B2 | 3/2015 | McCuen | |
| 8,968,276 B2 | 3/2015 | Zemlok et al. | |
| 8,968,337 B2 | 3/2015 | Whitfield et al. | |
| 8,992,422 B2 | 3/2015 | Spivey et al. | |
| 9,016,545 B2 | 4/2015 | Aranyi et al. | |
| 9,023,014 B2 | 5/2015 | Chowaniec et al. | |
| 9,033,868 B2 | 5/2015 | Whitman et al. | |
| 9,050,119 B2 * | 6/2015 | Devengenzo | A61B 34/71 |
| 9,055,943 B2 | 6/2015 | Zemlok et al. | |
| 9,064,653 B2 | 6/2015 | Prest et al. | |
| 9,072,515 B2 | 7/2015 | Hall et al. | |
| 9,113,847 B2 | 8/2015 | Whitman et al. | |
| 9,113,875 B2 | 8/2015 | Viola et al. | |
| 9,113,876 B2 | 8/2015 | Zemlok et al. | |
| 9,113,899 B2 | 8/2015 | Garrison et al. | |
| 9,216,013 B2 | 12/2015 | Scirica et al. | |
| 9,271,799 B2 * | 3/2016 | Shelton, IV | A61B 17/072 |
| 9,282,961 B2 | 3/2016 | Whitman et al. | |
| 9,282,963 B2 | 3/2016 | Bryant | |
| 9,295,522 B2 | 3/2016 | Kostrzewski | |
| 9,307,986 B2 | 4/2016 | Hall et al. | |
| 9,889,568 B2 * | 2/2018 | Kilroy | A61B 34/71 |
| 10,258,333 B2 | 4/2019 | Shelton, IV et al. | |
| 10,265,118 B2 * | 4/2019 | Gerhardt | A61B 18/1445 |
| 10,799,239 B2 | 10/2020 | Nicholas | |
| 11,504,123 B2 | 11/2022 | Nicholas | |
| 2001/0031975 A1 | 10/2001 | Whitman | |
| 2002/0049454 A1 | 4/2002 | Whitman et al. | |
| 2002/0165541 A1 | 11/2002 | Whitman | |
| 2003/0038938 A1 | 2/2003 | Jung et al. | |
| 2003/0165794 A1 | 9/2003 | Matoba | |
| 2004/0111012 A1 | 6/2004 | Whitman | |
| 2004/0133189 A1 | 7/2004 | Sakurai | |
| 2004/0153124 A1 | 8/2004 | Whitman | |
| 2004/0176751 A1 | 9/2004 | Weitzner et al. | |
| 2004/0193146 A1 | 9/2004 | Lee et al. | |
| 2005/0125027 A1 | 6/2005 | Knodel et al. | |
| 2005/0131442 A1 | 6/2005 | Yachia et al. | |
| 2006/0089533 A1 * | 4/2006 | Ziegler | A61B 1/00156 |
| | | | 600/114 |
| 2006/0142656 A1 | 6/2006 | Malackowski et al. | |
| 2006/0142740 A1 | 6/2006 | Sherman et al. | |
| 2006/0142744 A1 | 6/2006 | Boutoussov | |
| 2006/0259073 A1 | 11/2006 | Miyamoto et al. | |
| 2006/0278680 A1 | 12/2006 | Viola | |
| 2006/0284730 A1 | 12/2006 | Schmid et al. | |
| 2007/0005002 A1 * | 1/2007 | Millman | A61B 34/71 |
| | | | 604/30 |
| 2007/0023476 A1 | 2/2007 | Whitman et al. | |
| 2007/0023477 A1 | 2/2007 | Whitman et al. | |
| 2007/0029363 A1 | 2/2007 | Popov | |
| 2007/0084897 A1 | 4/2007 | Shelton et al. | |
| 2007/0102472 A1 | 5/2007 | Shelton | |
| 2007/0152014 A1 | 7/2007 | Gillum et al. | |
| 2007/0175947 A1 | 8/2007 | Ortiz et al. | |
| 2007/0175949 A1 | 8/2007 | Shelton et al. | |
| 2007/0175950 A1 | 8/2007 | Shelton, IV et al. | |
| 2007/0175951 A1 | 8/2007 | Shelton et al. | |
| 2007/0175955 A1 | 8/2007 | Shelton et al. | |
| 2007/0175961 A1 | 8/2007 | Shelton et al. | |
| 2007/0270784 A1 | 11/2007 | Smith et al. | |
| 2008/0029570 A1 | 2/2008 | Shelton et al. | |
| 2008/0029573 A1 | 2/2008 | Shelton et al. | |
| 2008/0029574 A1 | 2/2008 | Shelton et al. | |
| 2008/0029575 A1 | 2/2008 | Shelton et al. | |
| 2008/0058801 A1 | 3/2008 | Taylor et al. | |
| 2008/0109012 A1 | 5/2008 | Falco et al. | |
| 2008/0110958 A1 | 5/2008 | McKenna et al. | |
| 2008/0147089 A1 | 6/2008 | Loh et al. | |
| 2008/0167736 A1 | 7/2008 | Swayze et al. | |
| 2008/0185419 A1 | 8/2008 | Smith et al. | |
| 2008/0188841 A1 | 8/2008 | Tomasello et al. | |
| 2008/0197167 A1 | 8/2008 | Viola et al. | |
| 2008/0208195 A1 | 8/2008 | Shores et al. | |
| 2008/0237296 A1 | 10/2008 | Boudreaux et al. | |
| 2008/0251561 A1 | 10/2008 | Eades et al. | |
| 2008/0255413 A1 | 10/2008 | Zemlok et al. | |
| 2008/0255607 A1 | 10/2008 | Zemlok | |
| 2008/0262654 A1 | 10/2008 | Omori et al. | |
| 2008/0308603 A1 | 12/2008 | Shelton et al. | |
| 2008/0308604 A1 * | 12/2008 | Timm | A61B 17/07207 |
| | | | 227/180.1 |
| 2009/0012533 A1 | 1/2009 | Barbagli et al. | |
| 2009/0090763 A1 | 4/2009 | Zemlok et al. | |
| 2009/0099876 A1 | 4/2009 | Whitman | |
| 2009/0138006 A1 | 5/2009 | Bales et al. | |
| 2009/0171147 A1 | 7/2009 | Lee et al. | |
| 2009/0182193 A1 | 7/2009 | Whitman et al. | |
| 2009/0209990 A1 | 8/2009 | Yates et al. | |
| 2009/0254094 A1 | 10/2009 | Knapp et al. | |
| 2009/0289096 A1 * | 11/2009 | Shelton, IV | A61B 17/07207 |
| | | | 227/180.1 |
| 2009/0299141 A1 | 12/2009 | Downey et al. | |
| 2010/0001036 A1 * | 1/2010 | Marczyk | A61B 17/07207 |
| | | | 227/175.1 |
| 2010/0001306 A1 | 1/2010 | Park et al. | |
| 2010/0023022 A1 | 1/2010 | Zeiner et al. | |
| 2010/0069942 A1 | 3/2010 | Shelton, IV | |
| 2010/0179382 A1 * | 7/2010 | Shelton, IV | A61B 17/3205 |
| | | | 600/104 |
| 2010/0193568 A1 | 8/2010 | Scheib et al. | |
| 2010/0211053 A1 | 8/2010 | Ross et al. | |
| 2010/0225073 A1 | 9/2010 | Porter et al. | |
| 2011/0071508 A1 | 3/2011 | Duval et al. | |
| 2011/0077673 A1 | 3/2011 | Grubac et al. | |
| 2011/0121049 A1 | 5/2011 | Malinouskas et al. | |
| 2011/0125138 A1 | 5/2011 | Malinouskas et al. | |
| 2011/0139851 A1 | 6/2011 | McCuen | |
| 2011/0155783 A1 | 6/2011 | Rajappa et al. | |
| 2011/0155786 A1 | 6/2011 | Shelton, IV | |
| 2011/0172648 A1 | 7/2011 | Jeong | |
| 2011/0174099 A1 * | 7/2011 | Ross | A61B 17/115 |
| | | | 74/89.32 |
| 2011/0184245 A1 | 7/2011 | Kia et al. | |
| 2011/0204119 A1 | 8/2011 | McCuen | |
| 2011/0218522 A1 | 9/2011 | Whitman | |
| 2011/0276057 A1 | 11/2011 | Conlon et al. | |
| 2011/0290851 A1 * | 12/2011 | Shelton, IV | A61B 17/07207 |
| | | | 227/176.1 |
| 2011/0290854 A1 | 12/2011 | Timm et al. | |
| 2011/0295242 A1 * | 12/2011 | Spivey | A61B 17/07207 |
| | | | 606/1 |
| 2011/0295269 A1 | 12/2011 | Swensgard et al. | |
| 2011/0295270 A1 * | 12/2011 | Giordano | A61B 17/320092 |
| | | | 606/130 |
| 2012/0000962 A1 | 1/2012 | Racenet et al. | |
| 2012/0074199 A1 | 3/2012 | Olson et al. | |
| 2012/0089131 A1 | 4/2012 | Zemlok et al. | |
| 2012/0104071 A1 | 5/2012 | Bryant | |
| 2012/0116368 A1 | 5/2012 | Viola | |
| 2012/0143002 A1 | 6/2012 | Aranyi et al. | |
| 2012/0172924 A1 | 7/2012 | Allen, IV | |
| 2012/0205421 A1 * | 8/2012 | Shelton, IV | A61B 50/20 |
| | | | 227/177.1 |
| 2012/0211542 A1 | 8/2012 | Racenet | |
| 2012/0223121 A1 | 9/2012 | Viola et al. | |
| 2012/0245428 A1 | 9/2012 | Smith et al. | |
| 2012/0253329 A1 | 10/2012 | Zemlok et al. | |
| 2012/0310220 A1 | 12/2012 | Malkowski et al. | |
| 2012/0310221 A1 * | 12/2012 | Durant | A61B 34/30 |
| | | | 606/1 |
| 2012/0323226 A1 | 12/2012 | Chowaniec et al. | |
| 2012/0330285 A1 | 12/2012 | Hartoumbekis et al. | |
| 2013/0018361 A1 | 1/2013 | Bryant | |
| 2013/0093149 A1 | 4/2013 | Saur et al. | |
| 2013/0178838 A1 | 7/2013 | Malkowski | |
| 2013/0181035 A1 | 7/2013 | Milliman | |
| 2013/0184704 A1 | 7/2013 | Beardsley et al. | |

(56) References Cited

U.S. PATENT DOCUMENTS

| | | |
|---|---|---|
| 2013/0214025 A1 | 8/2013 | Zemlok et al. |
| 2013/0274722 A1 | 10/2013 | Kostrzewski et al. |
| 2013/0277409 A1 | 10/2013 | Marczyk |
| 2013/0282021 A1* | 10/2013 | Parihar .................. A61B 34/30 606/130 |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0005662 A1 | 1/2014 | Shelton, IV |
| 2014/0005678 A1* | 1/2014 | Shelton, IV ......... A61B 17/068 606/130 |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1* | 8/2014 | Scirica ............. A61B 17/00234 606/130 |
| 2014/0236174 A1 | 8/2014 | Williams et al. |
| 2014/0276932 A1 | 9/2014 | Williams et al. |
| 2014/0299647 A1* | 10/2014 | Scirica ............. A61B 17/07207 227/175.1 |
| 2014/0303668 A1* | 10/2014 | Nicholas .......... A61B 17/07207 606/207 |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0133957 A1 | 5/2015 | Kostrzewski |
| 2015/0136835 A1* | 5/2015 | Shelton, IV ..... A61B 17/07292 227/180.1 |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0282822 A1* | 10/2015 | Trees .................. A61B 17/282 606/41 |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1* | 12/2015 | Zergiebel ............ A61B 17/068 74/89.23 |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0000513 A1 | 1/2016 | Shelton, IV et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera |
| 2016/0113648 A1 | 4/2016 | Zergiebel et al. |
| 2016/0113649 A1 | 4/2016 | Zergiebel et al. |
| 2016/0175060 A1* | 6/2016 | Park ...................... A61B 34/30 606/130 |
| 2016/0249918 A1* | 9/2016 | Shelton, IV .......... A61B 90/70 227/175.1 |
| 2016/0296216 A1* | 10/2016 | Nicholas ................ A61B 17/00 |
| 2016/0296234 A1* | 10/2016 | Richard ................ A61B 17/34 |
| 2017/0211667 A1* | 7/2017 | Nicholas ............... A61B 34/71 |
| 2017/0281189 A1* | 10/2017 | Nalagatla ........... A61B 17/3211 |
| 2017/0296173 A1* | 10/2017 | Shelton, IV ......... A61B 17/068 |
| 2017/0319200 A1* | 11/2017 | Nicholas ............... A61B 34/71 |
| 2018/0125594 A1* | 5/2018 | Beardsley ........ A61B 17/07207 |
| 2019/0069917 A1* | 3/2019 | Sholev .................. A61B 34/00 |

FOREIGN PATENT DOCUMENTS

| | | |
|---|---|---|
| CN | 102247182 A | 11/2011 |
| CN | 104970884 A | 10/2015 |
| CN | 107019537 A | 8/2017 |
| DE | 102008053842 A1 | 5/2010 |
| EP | 0705571 A1 | 4/1996 |
| EP | 1769754 A1 | 4/2007 |
| EP | 1813212 A1 | 8/2007 |
| EP | 1980214 A2 | 10/2008 |
| EP | 2055243 A2 | 5/2009 |
| EP | 2100562 A2 | 9/2009 |
| EP | 2263568 A2 | 12/2010 |
| EP | 2316345 A1 | 5/2011 |
| EP | 2333509 A1 | 6/2011 |
| EP | 2649948 A1 | 10/2013 |
| EP | 2668910 A2 | 12/2013 |
| EP | 2937047 A1 | 10/2015 |
| EP | 3195812 A1 | 7/2017 |
| ES | 2333509 A1 | 2/2010 |
| JP | 08038488 | 2/1996 |
| JP | 2005125075 A | 5/2005 |
| KR | 20120022521 A | 3/2012 |
| WO | 2009039506 A1 | 3/2009 |
| WO | 2011108840 A2 | 9/2011 |
| WO | 2012040984 A1 | 4/2012 |

OTHER PUBLICATIONS

Extended European Search Report issued in European Application No. 17170006.5 dated Nov. 24, 2017.
Extended European Search Report corresponding to counterpart International Application No. EP 14 18 4882.0 dated May 12, 2015.
Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 97833 dated Sep. 3, 2015.
Extended European Search Report corresponding to counterpart International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.

(56) References Cited

OTHER PUBLICATIONS

European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Extended European Search Report corresponding to counterpart Int'l Appln. No. EP 16 16 4413.3 dated Dec. 8, 2016.
Chinese Office Action dated Sep. 30, 2020 for application No. 2017103218172 with English Translation.
Chinese Office Action for application No. 2017103218172 dated Apr. 30, 2021 with English Translation.
Chinese Office Action issued in corresponding Chinese Application No. 202111186169.7 dated Aug. 31, 2023, 16 pages.

* cited by examiner

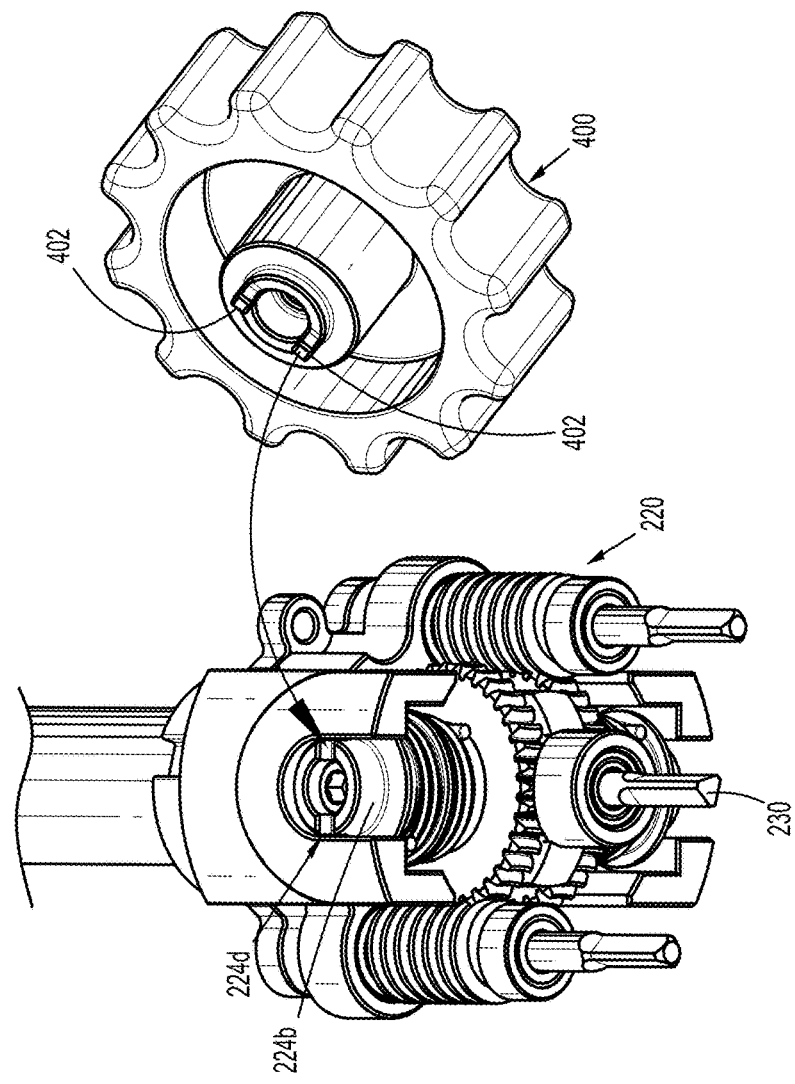
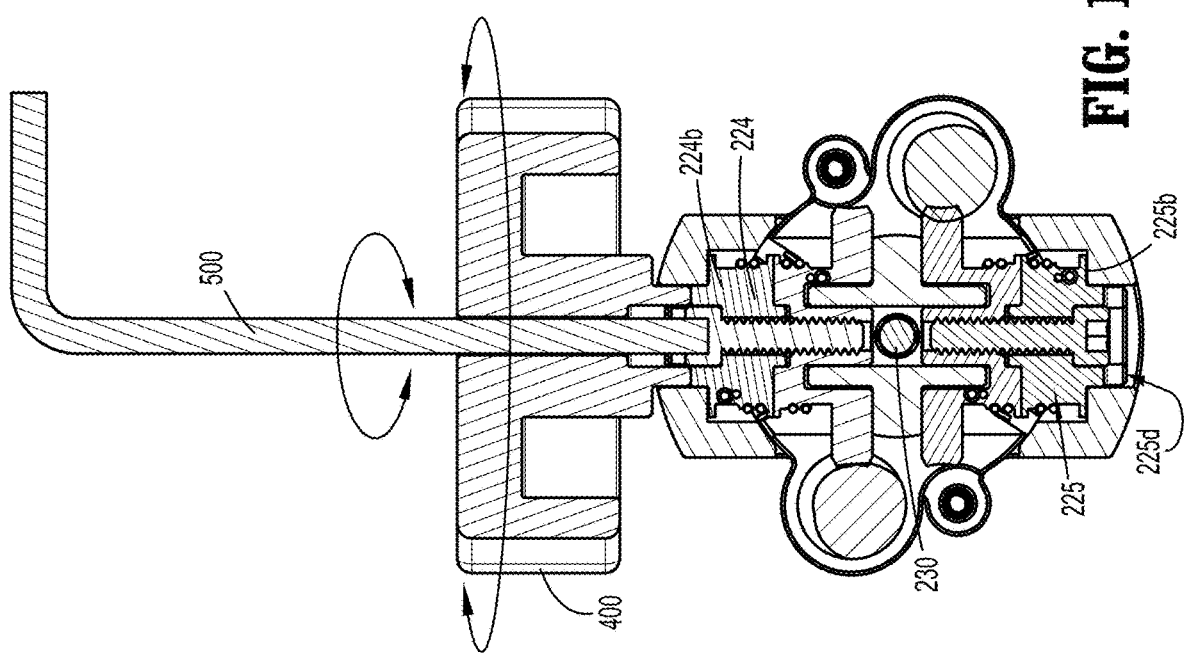
FIG. 14
FIG. 13

ADAPTER ASSEMBLY WITH PULLEY SYSTEM AND WORM GEAR DRIVE FOR INTERCONNECTING ELECTROMECHANICAL SURGICAL DEVICES AND SURGICAL END EFFECTORS

CROSS-REFERENCE TO RELATED APPLICATIONS

This application is a continuation of U.S. patent application Ser. No. 17/034,490, filed Sep. 28, 2020, which is a continuation of U.S. patent application Ser. No. 15/491,268, filed Apr. 19, 2017, now U.S. Pat. No. 10,799,239, which claims the benefit of U.S. Provisional Patent Application Ser. No. 62/333,584, filed May 9, 2016, the entire contents of each of which are incorporated by reference herein.

TECHNICAL FIELD

The present disclosure relates to adapter assemblies for use in surgical systems. More specifically, the present disclosure relates to adapter assemblies for use with, and to electrically and mechanically interconnect, electromechanical surgical devices and surgical end effectors, and to surgical systems including handheld electromechanical surgical devices and adapter assemblies for connecting surgical end effectors to the handheld electromechanical surgical devices.

BACKGROUND

A number of surgical device manufacturers have developed product lines with proprietary powered drive systems for operating and/or manipulating a surgical device. In many instances the surgical devices include a powered handle assembly, which is reusable, and a disposable end effector or the like that is selectively connected to the powered handle assembly prior to use and then disconnected from the end effector following use in order to be disposed of or in some instances, sterilized for re-use.

Many of the existing end effectors for use with many of the existing powered surgical devices and/or handle assemblies are driven by a linear force. For example, end effectors for performing endo-gastrointestinal anastomosis procedures, end-to-end anastomosis procedures and transverse anastomosis procedures, each typically require a linear driving force in order to be operated. These end effectors are not compatible with surgical devices and/or handle assemblies that use a rotary motion to deliver power or the like.

In order to make the linear driven end effectors compatible with powered surgical devices and/or handle assemblies that use a rotary motion to deliver power, adapters and/or adapter assemblies are used to interface between and interconnect the linear driven end effectors with the powered rotary driven surgical devices and/or handle assemblies. Many of these adapter and/or adapter assemblies are complex devices including many parts and requiring extensive labor to assemble.

Adapter concepts often include a cable system for distal rotation and/or articulation. Some designs of cable systems include pulleys or lead screws with counter-directional threads to generate linear motion. Consistent with stroke dynamics, lead screw designs can require additional length to accommodate coordinated cable take-up and release. By comparison, pulley designs can be more compact than lead screw designs, but typically require different considerations including those associated with assembly and tensioning.

Accordingly, a need exists to develop adapters and/or adapter assemblies that incorporate fewer parts, are less labor intensive to assemble, and are ultimately more economical to manufacture. Specifically, a need exits to develop such adapters and/or adapter assemblies with improved pulley designs that simplify manufacturing and assembly as well as improve cable tensioning.

SUMMARY

According to an aspect of the present disclosure, an adapter assembly is provided. The adapter assembly selectively interconnects an end effector that is configured to perform a function and a surgical device that is configured to operate the end effector. The adapter assembly includes an outer tube having a distal end and a proximal end, a housing secured to the proximal end of the outer tube, and a cable drive assembly supported by the housing.

The cable drive assembly includes a worm gear, a cable gear coupled to the worm gear and rotatable in response to rotation of the worm gear, a capstan coupled to the cable gear and rotatable in response to rotation of the cable gear, and a cable coupled to the capstan. The cable may be axially translatable in response rotation of the capstan to actuate a function of the end effector while connected to the distal end of the outer tube.

In certain embodiments of the adapter assembly, the cable drive assembly may include a second worm gear, a second cable gear coupled to the second worm gear, a second capstan coupled to the second cable gear, and a second cable coupled to the second capstan. The second cable may be axially translatable in response to rotation of one or more of the second worm gear, the second cable gear, and the second capstan.

In some embodiments of the adapter assembly, the cable drive assembly may further include one or more pulleys supporting the cable and configured to direct the cable into the outer tube.

In certain embodiments of the adapter assembly, the cable drive assembly may further include a body portion that supports the worm gear and the cable gear in contacting relation with one another.

The adapter assembly may further include a firing assembly that extends through the cable drive assembly and into the outer tube. In some embodiments, the firing assembly may include a firing shaft that rotates independent of the cable drive assembly to actuate a firing function of the end effector.

The housing of the adapter assembly may include an outer housing and an inner housing that support the cable drive assembly therein.

In some embodiments of the adapter assembly, the outer tube defines a longitudinal axis that extends between the proximal and distal ends of the outer tube. The worm gear may be supported on a shaft member that extends in parallel relationship to the longitudinal axis of the outer tube. The shaft member may be rotatable to rotate the worm gear.

According to another aspect of the present disclosure, a surgical stapling apparatus is provided. The surgical stapling apparatus includes an end effector, a surgical device configured to operate the end effector, and an adapter assembly for selectively interconnecting the end effector and the surgical device.

The adapter assembly of the surgical stapling apparatus includes an outer tube having a distal end and a proximal end, a housing secured to the proximal end of the outer tube, and a cable drive assembly supported by the housing. The cable drive assembly includes a worm gear, a cable gear coupled to the worm gear, a capstan coupled to the cable gear, and a cable coupled to the capstan. The cable may be axially translatable in response rotation of one or more of the worm gear, the cable gear, and the capstan.

The adapter assembly of the surgical stapling apparatus may further include a firing assembly that extends through the cable drive assembly and into the outer tube. The firing assembly may include a firing shaft that rotates independent of the cable drive assembly to actuate a firing function of the end effector.

In some embodiments of the surgical stapling apparatus, the cable drive assembly may further include a second worm gear, a second cable gear coupled to the second worm gear, a second capstan coupled to the second cable gear, and a second cable coupled to the second capstan. The second cable may be axially translatable in response to rotation of one or more of the second worm gear, the second cable gear, and the second capstan.

In certain embodiments of the surgical stapling apparatus, the housing of the adapter assembly may include an outer housing and an inner housing. The inner and outer housings may support the cable drive assembly therein.

In some embodiments of the surgical stapling apparatus, the cable drive assembly may further include one or more pulleys supporting the cable and configured to direct the cable into the outer tube.

In certain embodiments of the surgical stapling apparatus, the cable drive assembly may further include a body portion that supports the worm gear and the cable gear in contacting relation with one another.

In some embodiments of the surgical stapling apparatus, the outer tube of the adapter assembly defines a longitudinal axis that extends between the proximal and distal ends of the outer tube. The worm gear may be supported on a shaft member that extends in parallel relationship to the longitudinal axis of the outer tube. The shaft member may be rotatable to rotate the worm gear.

According to yet another aspect of the present disclosure, an adapter assembly for selective connection to a surgical device is provided. The adapter assembly includes an outer tube having a distal end and a proximal end, a housing secured to the proximal end of the outer tube, and a cable drive assembly supported by the housing. The cable drive assembly includes a worm gear drive assembly, a cable gear assembly coupled to the worm gear drive assembly, and one or more cables coupled to the cable gear assembly and axially translatable within the outer tube.

In some embodiments, the cable drive assembly may further include a second worm gear, a second cable gear coupled to the second worm gear, a second capstan coupled to the second cable gear, and a second cable coupled to the second capstan.

Further details and aspects of exemplary embodiments of the present disclosure are described in more detail below with reference to the appended figures.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 13 is a cross-sectional view of FIG. 11 as taken along section line 13-13 shown in FIG. 12; and FIG. 14 is a perspective view of the drive system of FIG. 7 and of a tensioning device.

DETAILED DESCRIPTION

Figure 1:
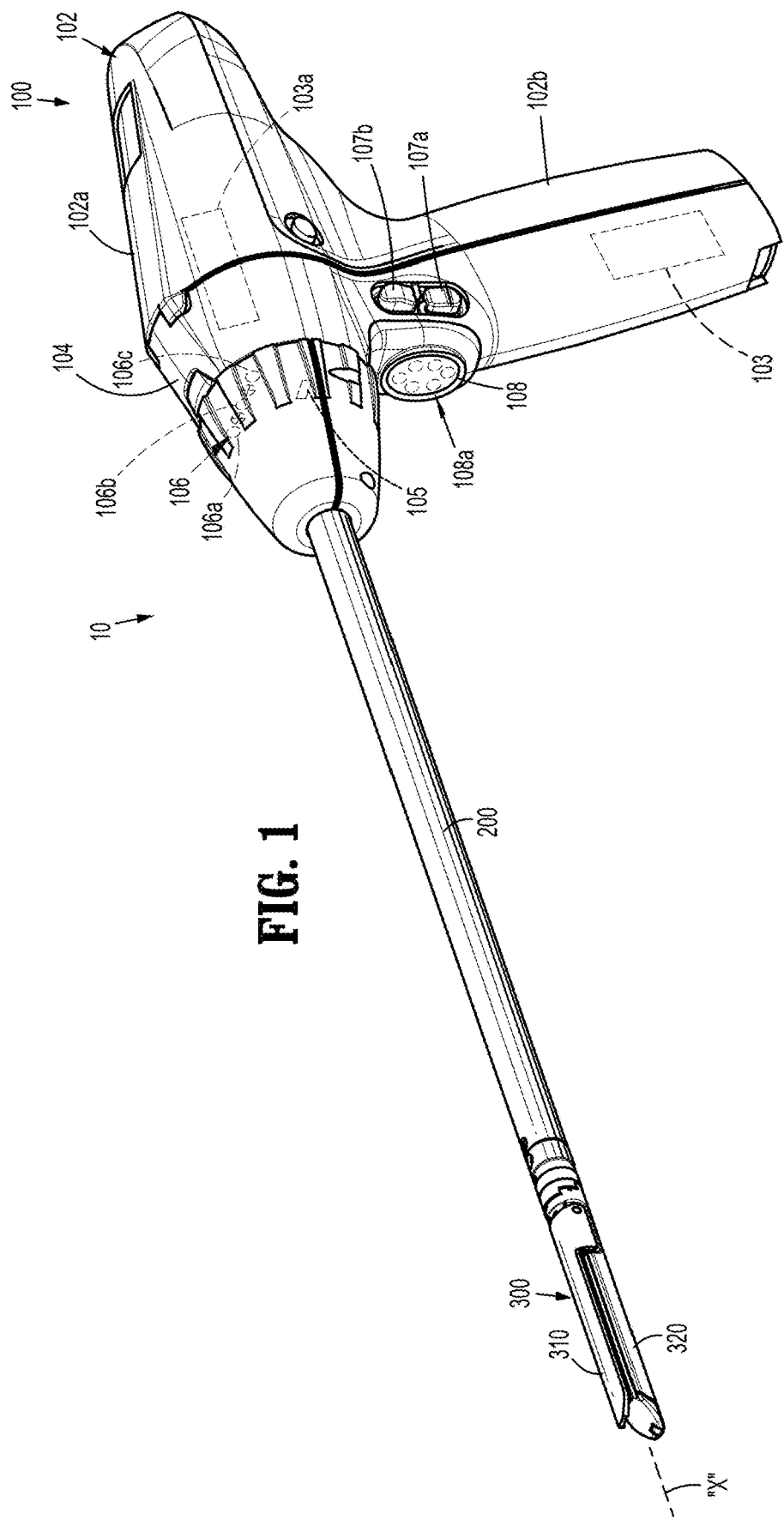
FIG. 1 is a perspective view of an electromechanical surgical system in accordance with the principles of the present disclosure.

Electromechanical surgical systems of the present disclosure include surgical devices in the form of powered handheld electromechanical instruments configured for selective attachment to a plurality of different end effectors that are each configured for actuation and manipulation by the powered handheld electromechanical surgical instrument. In particular, the presently described electromechanical surgical systems include adapter assemblies that interconnect the powered handheld electromechanical surgical instruments to the plurality of different end effectors. Each adapter assembly includes an articulation assembly and a firing assembly that is operatively coupled to a powered handheld electromechanical surgical instrument for effectuating actuation and/or manipulation of the plurality of different end effectors.

Embodiments of the presently disclosed electromechanical surgical systems, surgical devices/handle assemblies, adapter assemblies, and/or end effectors/loading units are described in detail with reference to the drawings, in which like reference numerals designate identical or corresponding elements in each of the several views. As used herein the term "distal" refers to that portion of the system, assembly, device, and/or component thereof, farther from the user, while the term "proximal" refers to that portion of the system, assembly, device, and/or component thereof, closer to the user.

Turning now to FIG. 1, an electromechanical surgical system, in accordance with the present disclosure, generally referred to as 10, includes a surgical device 100 in the form of a powered handheld electromechanical instrument, an adapter assembly 200, and a surgical loading unit (e.g., multiple- or single-use loading unit) or end effector 300. Surgical device 100 is configured for selective connection with adapter assembly 200, and, in turn, adapter assembly 200 is configured for selective connection with end effector 300. Together, surgical device 100 and adapter assembly 200 may cooperate to actuate end effector 300.

Surgical device 100 of electromechanical surgical system 10 includes a handle housing 102 including a controller or circuit board (not shown) and a drive mechanism 106 situated therein. The circuit board is configured to control the various operations of surgical device 100. Handle housing 102 defines a cavity therein (not shown) for selective removable receipt of a rechargeable battery 103 therein. The battery 103 is configured to supply power to any electrical components of surgical device 100. The drive mechanism 106 within the handle housing 102 is configured to drive rotatable shafts 106a-106c (and/or gear components—not shown) within handle housing 102 in order to perform the various operations of surgical device 100. In particular, drive mechanism 106 (and/or components thereof) is operable to selectively articulate end effector 300 about a longitudinal axis "X" and relative to a distal end of adapter assembly 200, to selectively rotate end effector 300 about longitudinal axis "X" and relative to handle housing 102, to selectively move/approximate/separate an anvil assembly 310 and a cartridge assembly 320 of end effector 300 relative to one another, and/or to fire a stapling and cutting cartridge within cartridge assembly 320 of end effector 300.

Handle housing 102 of surgical device 100 includes an upper housing portion 102a that houses various components of surgical device 100, and a lower hand grip portion 102b extending from upper housing portion 102a. Lower hand grip portion 102b of handle housing 102 may be disposed distally of a proximal-most end of upper housing portion 102a of handle housing 102. The location of lower hand grip portion 102b relative to upper housing portion 102a is selected to balance a weight of surgical device 100 while surgical device 100 is connected to or supports adapter assembly 200 and/or end effector 300.

A connection portion 104 of handle housing 102 is configured to secure to a proximal end of adapter assembly 200. Connection portion 104 houses an articulation contact surface 105 in electrical communication with the circuit board (not shown) of surgical device 100 to control drive mechanism 106. Each rotatable drive shaft 106a-106c of drive mechanism 106 can be independently, and/or dependently, actuatable and rotatable. In embodiments, rotatable drive shafts, 106a, 106b, and 106c may be arranged in a common plane or line with one another. As can be appreciated, any number of rotatable drive shafts can be arranged in any suitable configuration.

Handle housing 102 of surgical device 100 supports finger-actuated control buttons, rocker devices, and/or the like for activating various functions of surgical device 100. For example, handle housing 102 may support actuators including an actuation pad 108 in operative registration with sensors 108a that cooperate with actuation pad 108 to effectuate, for instance, opening, closing, and/or firing of end effector 300. Handle housing 102 can support actuators 107a, 107b which can be disposed in electrical communication with one or more motors (not shown) of drive mechanism 106 to effectuate rotation of rotatable drive shafts 106a, 106b, and/or 106c for actuation thereof to enable adjustment of one or more of the components of adapter assembly 200. Any of the presently described actuators can have any suitable configuration (e.g., button, knob, toggle, slide, etc.).

Reference may be made to International Application No. PCT/US2008/077249, filed Sep. 22, 2008 (Inter. Pub. No. WO 2009/039506), and U.S. Patent Application Publication No. 2011/0121049, filed on Nov. 20, 2009, the entire contents of each of which being incorporated herein by reference, for a detailed description of various internal components of and operation of exemplary electromechanical surgical systems, the components of which are combinable and/or interchangeable with one or more components of electromechanical surgical systems 10 described herein.

Figure 2:
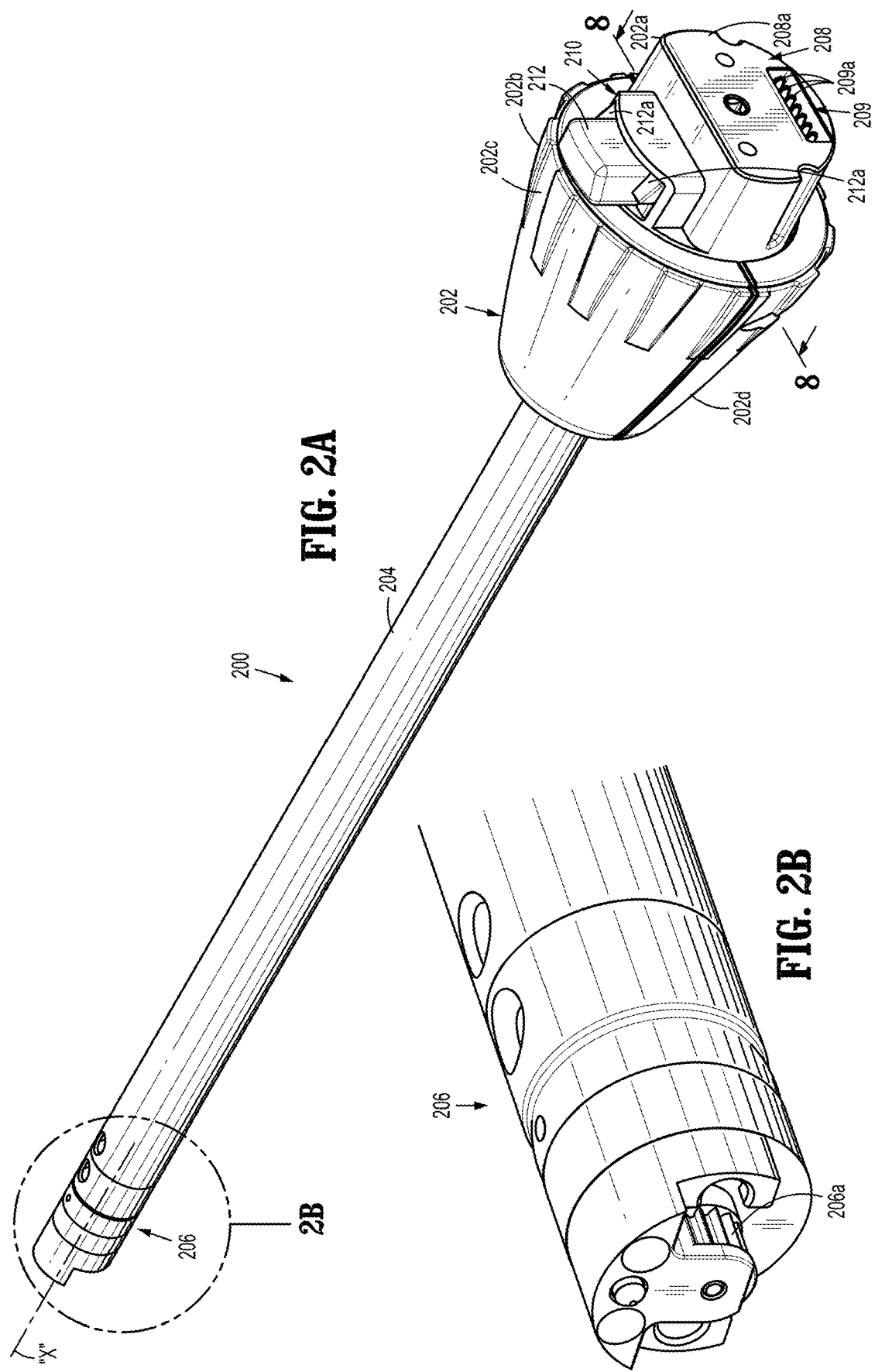
FIG. 2A is a perspective view of an adapter assembly of the electromechanical surgical system of FIG. 1.
FIG. 2B is a perspective view of the indicated area of detail shown in FIG. 2A.
Figure 3:
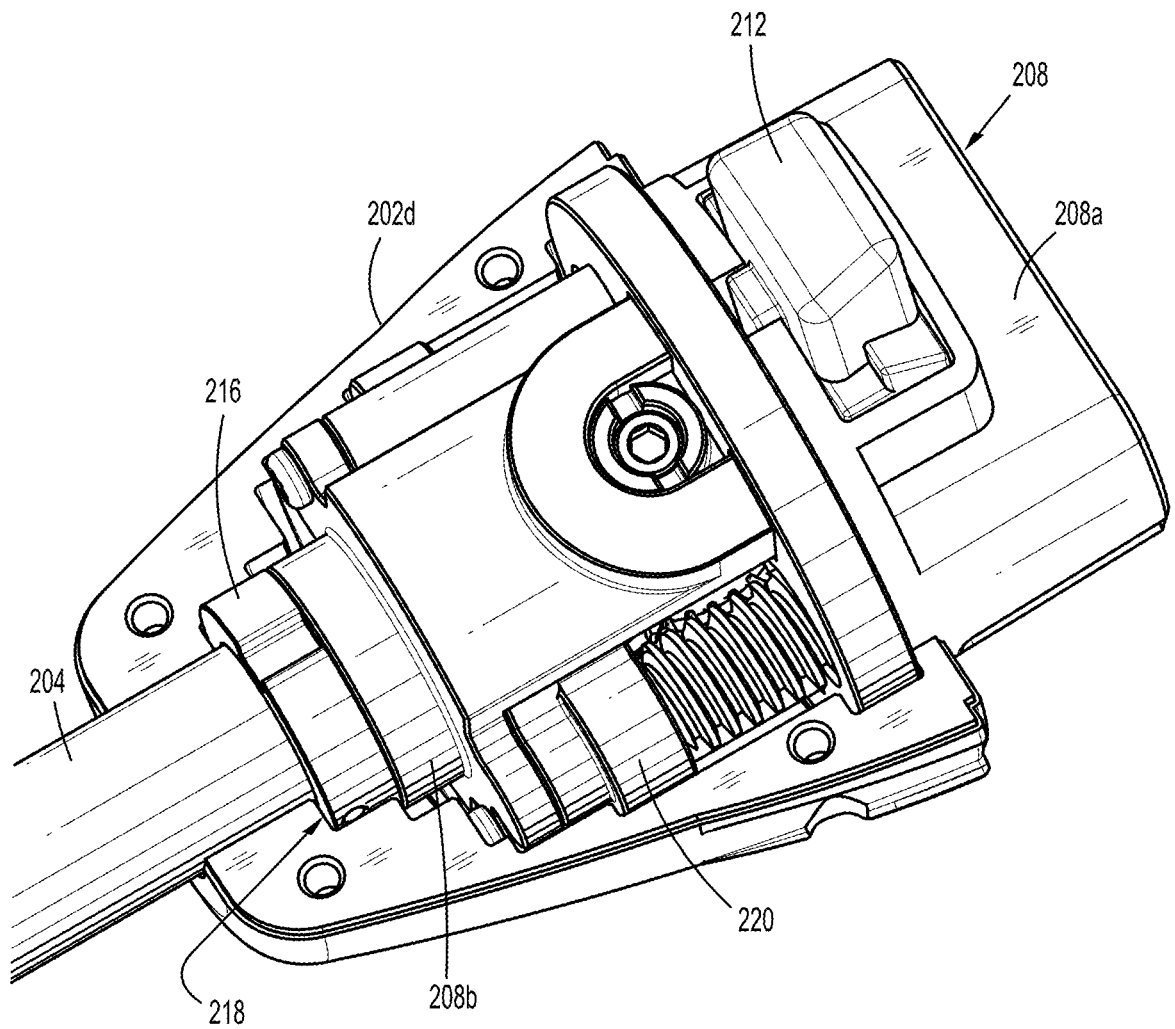
FIG. 3 is an enlarged, top, perspective view of a proximal portion of the adapter assembly of FIG. 2, the proximal portion of the adapter assembly shown with a portion of an outer housing thereof removed for clarity.
Figure 4:
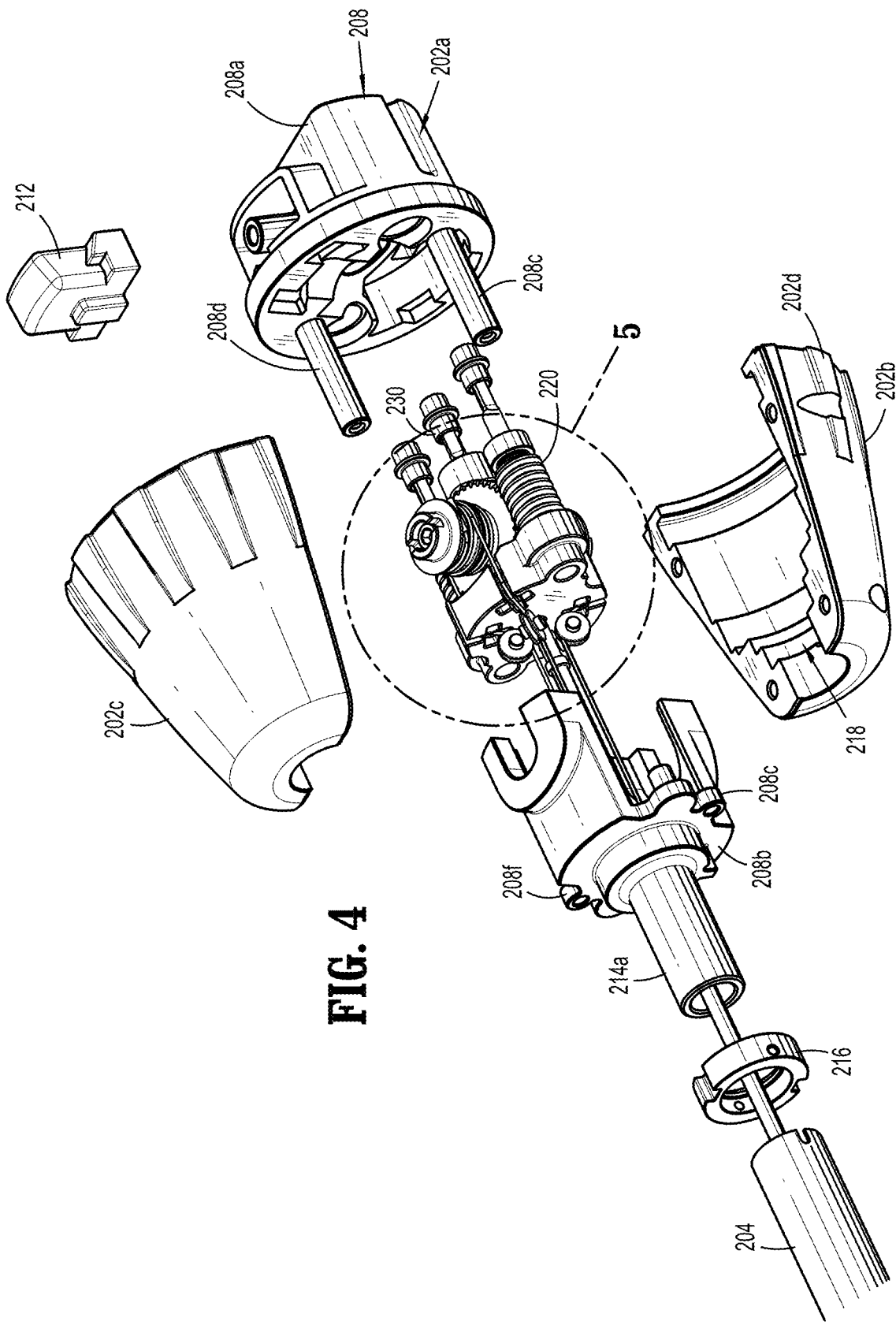
FIG. 4 is a perspective view, with parts separated, of the proximal portion of the adapter assembly of FIG. 2.

With reference to FIGS. 2A and 2B, adapter assembly 200 of electromechanical surgical system 10 includes a housing 202 at a proximal end portion thereof and an outer tube 204 that extends distally from housing 202 along longitudinal axis "X" to a distal end portion 206. Distal end portion 206 of outer tube 204 couples a distal end of adapter assembly 200 to a proximal end of end effector 300. Reference can be made to U.S. Patent Application Publication No. 2015/0297199, filed Apr. 21, 2014 for a detailed description of exemplary distal end portions, the entire contents of which are incorporated herein as discussed above. As described in U.S. Patent Application Publication No. 2015/0297199, the distal end portion may support a gimbal or the like that couple to an articulation assembly such as the articulation or cable drive assembly described herein to enable end effectors, such as end effector 300 of electromechanical surgical system 10, to articulate relative to adapter assembly 200 of electromechanical surgical system 10. Such distal end portions 206 may support a rotatable gear 206a that engages with a proximal end of end effector 300 to effectuate a firing thereof as described in greater detail below.

Referring to FIGS. 2A-4, housing 202 of adapter assembly 200 includes an inner housing 202a and an outer housing 202b having first and second housing halves 202c, 202d. Inner housing 202a includes a housing body 208 having a proximal housing body 208a and a distal housing body 208b that couple together via fastener-receiving arms 208c, 208d of proximal housing body 208a and fastener-receiving ears 208e, 208f of distal housing body 208b. Proximal housing body 208a of inner housing 202a supports an electrical assembly 209 therein and a mounting assembly 210 thereon.

Electrical assembly 209 of housing 202 may include a circuit board with contact pins 209a for electrical connection to a corresponding electrical plug (not shown) disposed in connection portion 104 of surgical device 100 (e.g., for calibration and communication of life-cycle information to the circuit board of the surgical device 100).

Mounting assembly 210 of housing 202 includes a mounting button 212 that is biased in an extended position and is configured to be depressed downwardly to a compressed position. In the compressed position, mounting button 212 is disposed in close approximation with housing body 208 of inner housing 202a and offset from the extended position thereof. Mounting button 212 includes sloped engagement features 212a that are configured to contact connection portion 104 (FIG. 1) of handle housing 102 while mounting button 212 is in the extended position to facilitate securement of housing 202 of adapter assembly 200 to connection portion 104 of handle housing 102. For a detailed description of similar electrical and mounting assemblies, reference can be made to U.S. Patent Application Publication No.

2015/0157320, filed Nov. 21, 2014 m the entire contents of which are incorporated by reference herein.

Outer housing 202b of housing 202 is disposed around inner housing 202a of housing 202 to support an articulation or cable drive assembly 220 and a firing assembly 230 within housing 202 of adapter assembly 200. Distal housing body 208b of inner housing 208 includes a distal shaft 214a that is received within a proximal end of outer tube 204 and coupled thereto by a bearing 216 mounted within a channel 218 defined within outer housing 202b of housing 202.

Figure 6:
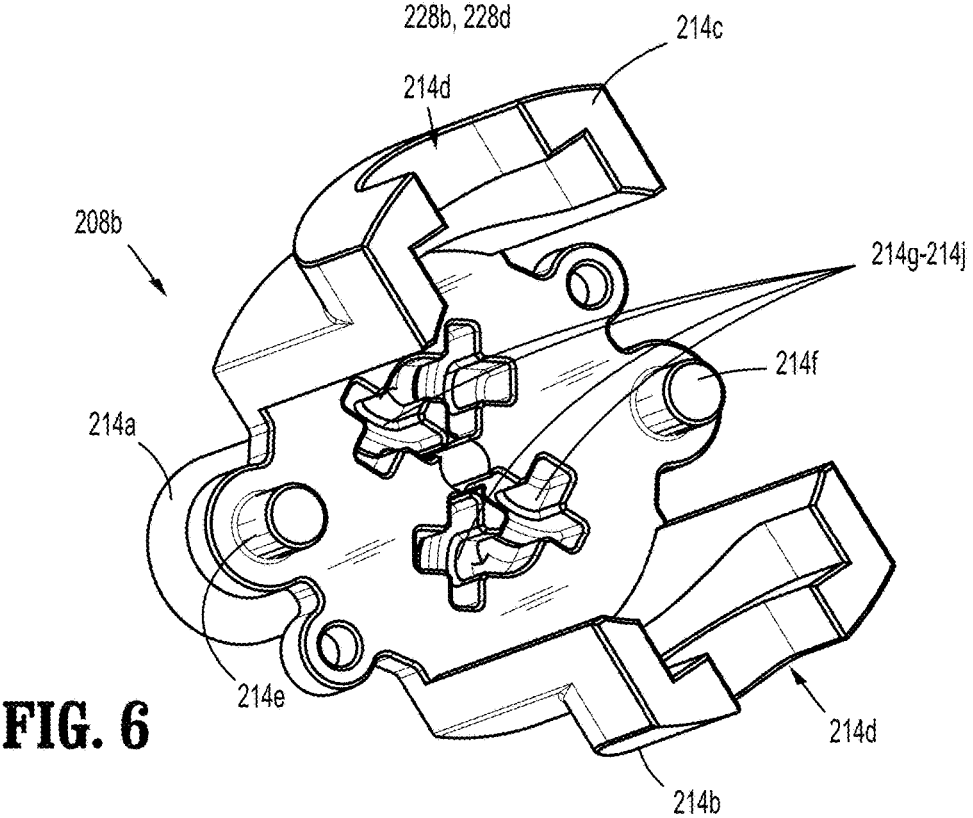
FIG. 6 is an enlarged, perspective view of a distal housing of the adapter assembly of FIG. 2.

As seen in FIG. 6, distal housing body 208b further includes mirrored arms 214b, 214c each defining a U-shaped passage 214d. U-shaped passages 214d of distal housing body 208b extend through arms 214b, 214c of distal housing body 208b and are configured to receive first and second cable gear assemblies 224, 225 of cable drive assembly 220 therein. Distal housing body 208b also includes pins or bosses 214e, 214f that extend proximally from a proximal surface of distal housing body 208b. The proximal surface of distal housing body 208b also defines distal pulley recesses 214g-214j therein.

With reference to FIGS. 5-7 and 10, cable drive assembly 220 includes a body portion 222, a first cable gear assembly 224, a second cable gear assembly 225, a first worm gear drive assembly 226, and a second worm gear drive assembly 227, proximal guide pulleys 228a-228d, and distal guide pulleys 229a-229d.

Body portion 222 of cable drive assembly 220 defines proximal pulley recesses 222a-222d that receive respective proximal guide pulleys 228a-228d therein to enable the respective proximal guide pulleys 228a-228d to rotate therein as cables 240a, 240b of cable drive assembly 220 rotate around respective proximal guide pulleys 228a-228d to manipulate end effector 300. Similarly, distal guide pulleys 229a-229d of cable drive assembly 220 are received within respective distal pulley recesses 214g-214j of distal housing body 208b of inner housing 202a to enable distal guide pulleys 229a-229d to rotate therein as cables 240a, 240b of cable drive assembly 220 rotate around respective distal guide pulleys 229a-229d to manipulate end effector 300.

Body portion 222 of cable drive assembly 220 includes an upper mounting projection 222e extending therefrom and positioned to partially receive first cable gear assembly 224 of cable drive assembly 220 therein for supporting first cable gear assembly 224 on upper mounting projection 222e of body portion 222. A lower mounting projection 222f (see FIG. 8) also extends from body portion 222 of cable drive assembly 220 in a direction opposite upper mounting projection 222e of body portion 222. Lower mounting projection 222f of body portion 222 is positioned to support second cable gear assembly 225 of cable drive assembly 220 thereon. Body portion 222 of cable drive assembly 220 further defines worm gear recesses 222g, 222h therein that rotatably receive first and second worm drive assemblies 226, 227, respectively in a proximal end thereof and pins 214e, 214f of distal housing body 208b in a distal end thereof. A firing shaft passage 222i is defined centrally through body portion 222 to receive a firing assembly 230 therein.

Figure 5:
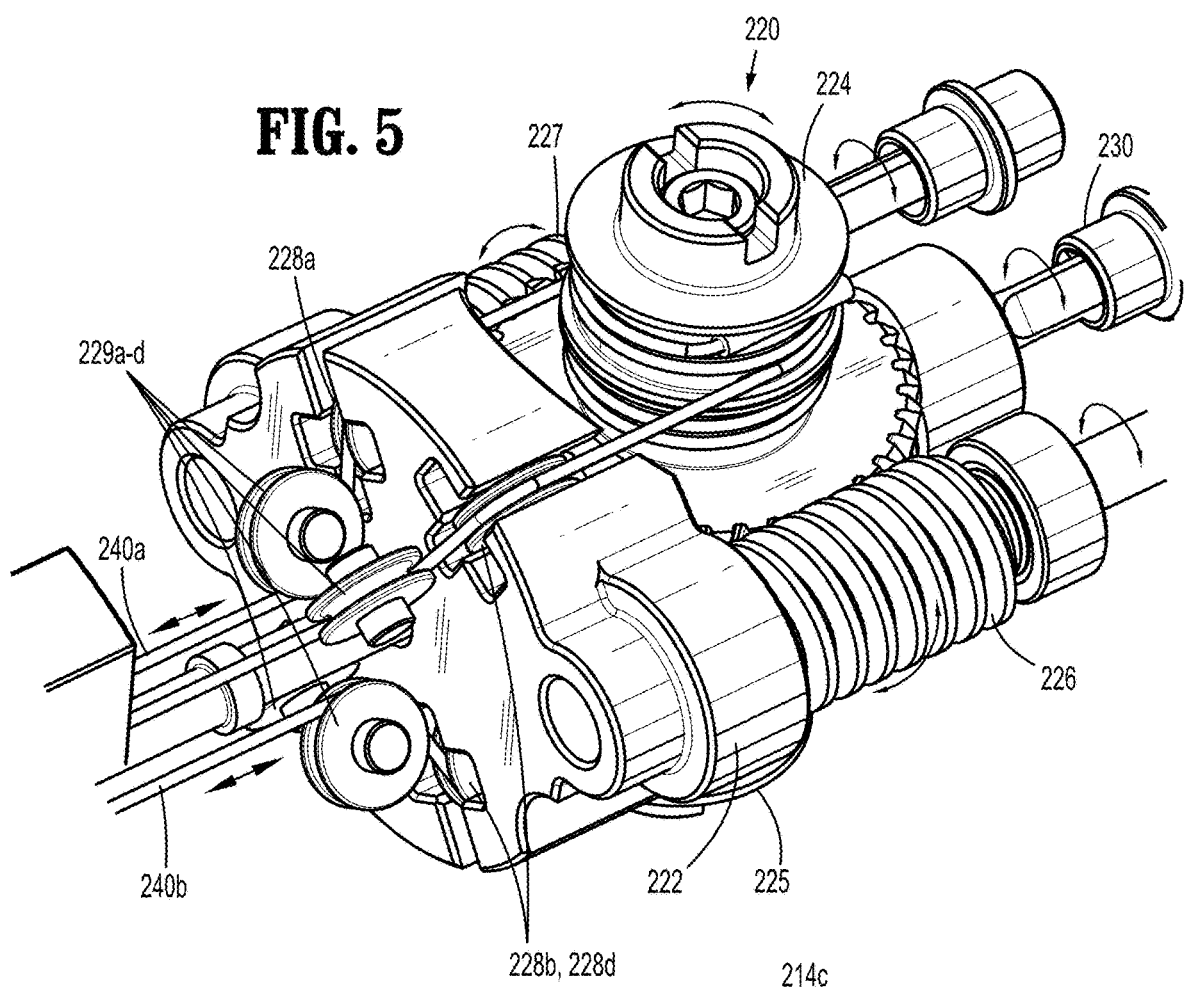
FIG. 5 is an enlarged, perspective view, of the indicated area of detail shown in FIG. 4.
Figure 7:
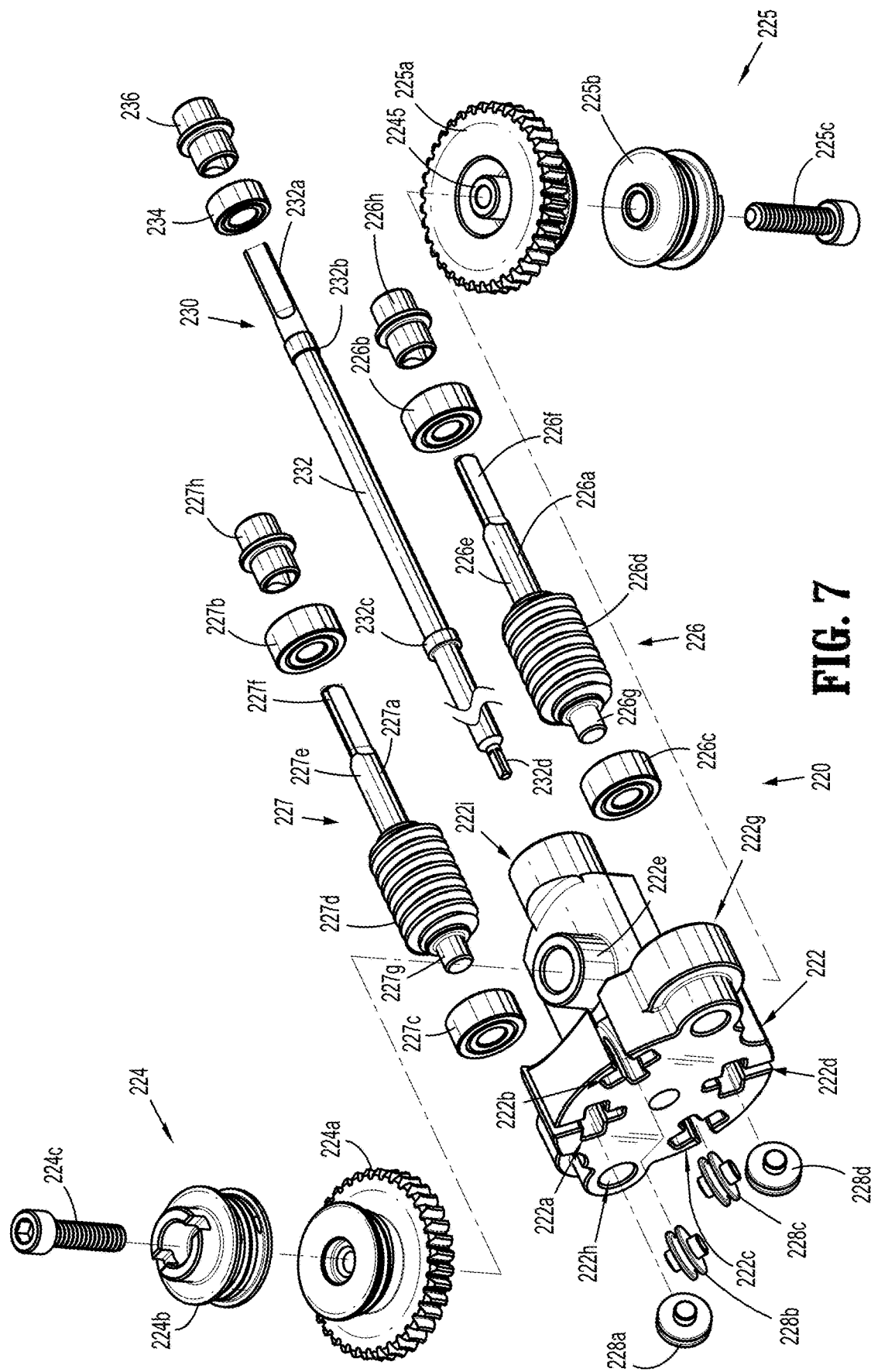
FIG. 7 is a perspective view, with parts separated, of a drive system of the adapter assembly of FIG. 2.
Figure 8:
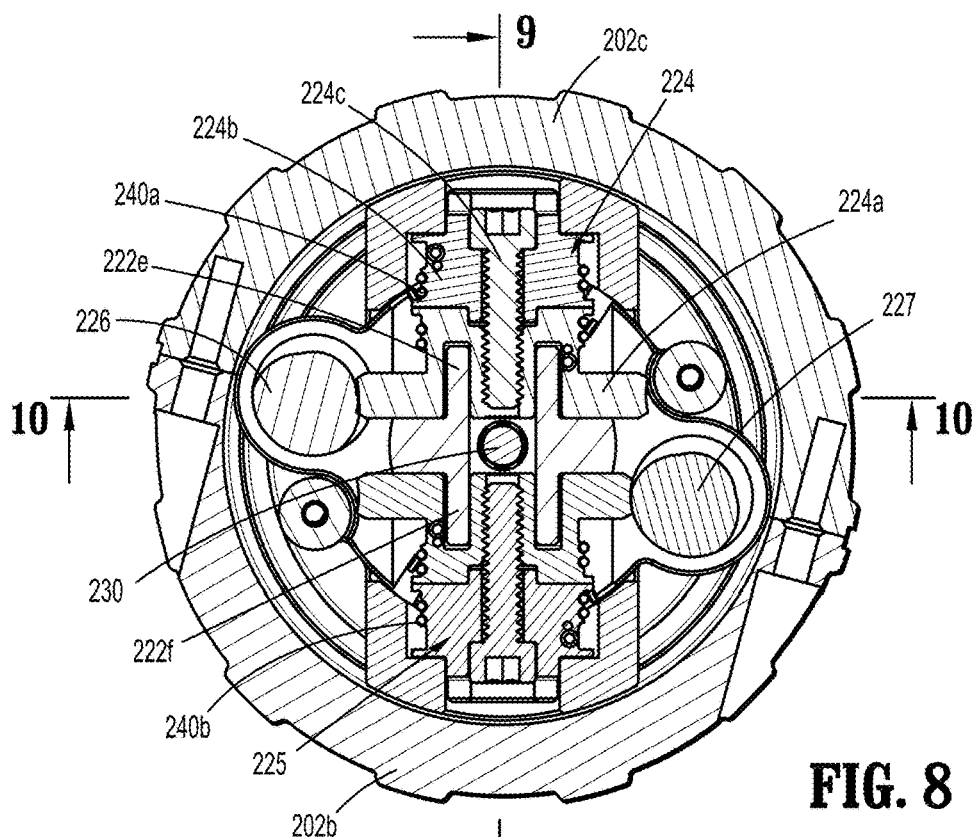
FIG. 8 is a cross-sectional view of the adapter assembly of FIG. 2 as taken along section line 8-8 shown in FIG. 2.

Referring to FIGS. 5, 7 and 8, first cable gear assembly 224 of cable drive assembly 220 includes an upper gear 224a, an upper capstan 224b supported on upper gear 224a, and an upper fastener 224c that couples upper capstan 224b to upper gear 224a while upper capstan 224b is coupled to upper mounting projection 222e of body portion 222 of cable drive assembly 220. Similarly, second cable gear assembly 225, which mirrors first cable gear assembly 224, includes a lower gear 225a, a lower capstan 225b supported on lower gear 225a, and a lower fastener 225c that couples lower capstan 225b to lower gear 225a while lower capstan 225b is coupled to lower mounting projection 222f of body portion 222 of cable drive assembly 220. Each of upper and lower gears 224a, 225a of respective first and second gear assemblies 224, 225 include a center protuberance 2245 that is received in respective upper and lower mounting projections 222e, 222f of body portion 222 to enable respective first and second gear assemblies 224, 225 to rotate about respective upper and lower mounting projections 222e, 222f of body portion 222. First and second cables 240a, 240b are wound around respective upper and lower capstans 224b, 225b and around respective proximal and distal guide pulleys 228a-228d, 229a-229d so that opposite ends/sides of each of the respective cables 240a, 240b extends distally through outer tube 204 to operatively couple to end effector 300 (e.g., to effectuate rotation and/or articulation thereof).

First worm gear drive assembly 226 of cable drive assembly 220 includes a first worm drive 226a rotatably supported between bearings 226b, 226c. First worm drive 226a includes a worm gear 226d secured on a shaft member 226e. Shaft member 226e has a proximal driving end 226f received in bearing 226b and a distal end 226g received in bearing 226c.

Similarly, second worm gear drive assembly 227 of cable drive assembly 220 includes a first worm drive 227a rotatably supported between bearings 227b, 227c. Second worm drive 227a includes a worm gear 227d secured on a shaft member 227e. Shaft member 227e has a proximal driving end 227f received in bearing 227b and a distal end 227g received in bearing 227c.

Figure 9:
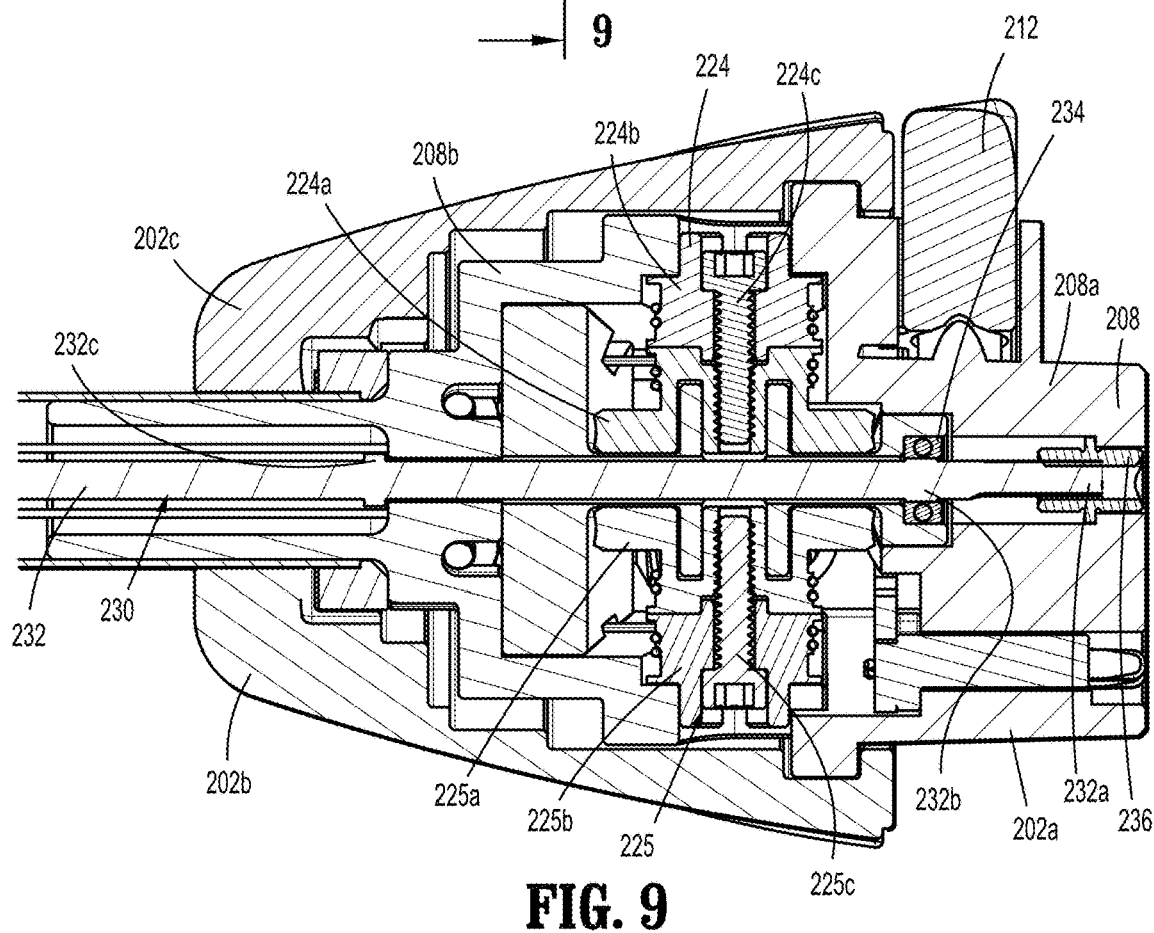
FIG. 9 is a cross-sectional view of a portion of the adapter assembly of FIG. 2 as taken along section line 9-9 shown in FIG. 8.
Figure 10:
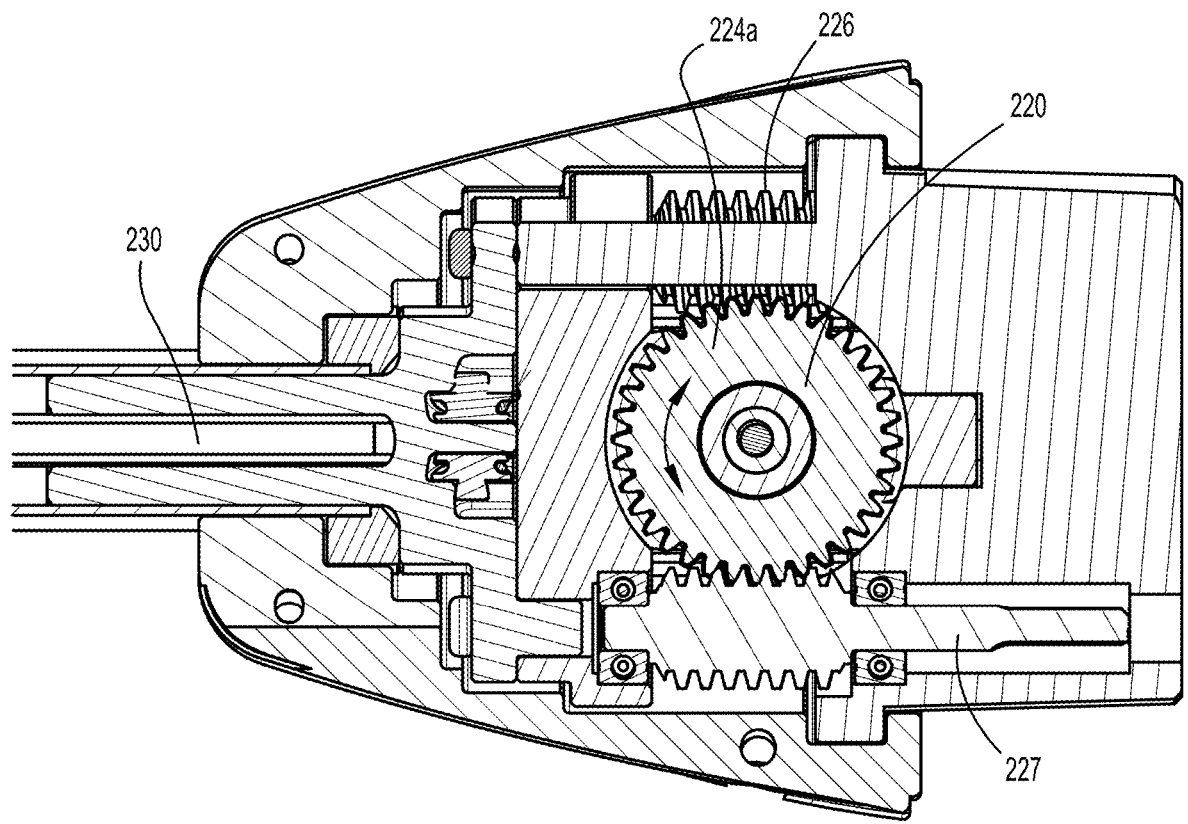
FIG. 10 is a cross-sectional view of a portion of the adapter assembly of FIG. 2 as taken along section line 10-10 shown in FIG. 8.

Referring to FIGS. 7, 9, and 10, firing assembly 230 of adapter assembly 200 includes a firing shaft 232, a bearing 234 supported on firing shaft 232, and an input socket 236 secured to a proximal end 232a of firing shaft 232. Firing shaft 232 of firing assembly 230 includes spaced collars 232b, 232c and a distal driving end 232d. Collar 232b of firing shaft 232 supports bearing 234 thereon and collar 232c of firing shaft 232 supports firing shaft 232 against distal housing body 208b of inner housing 202a. Distal driving end 232d of firing shaft 232 is extends to distal end portion 206 of outer tube 204 to effectuate a firing of end effector 300 as described in greater detail below.

Figure 11:
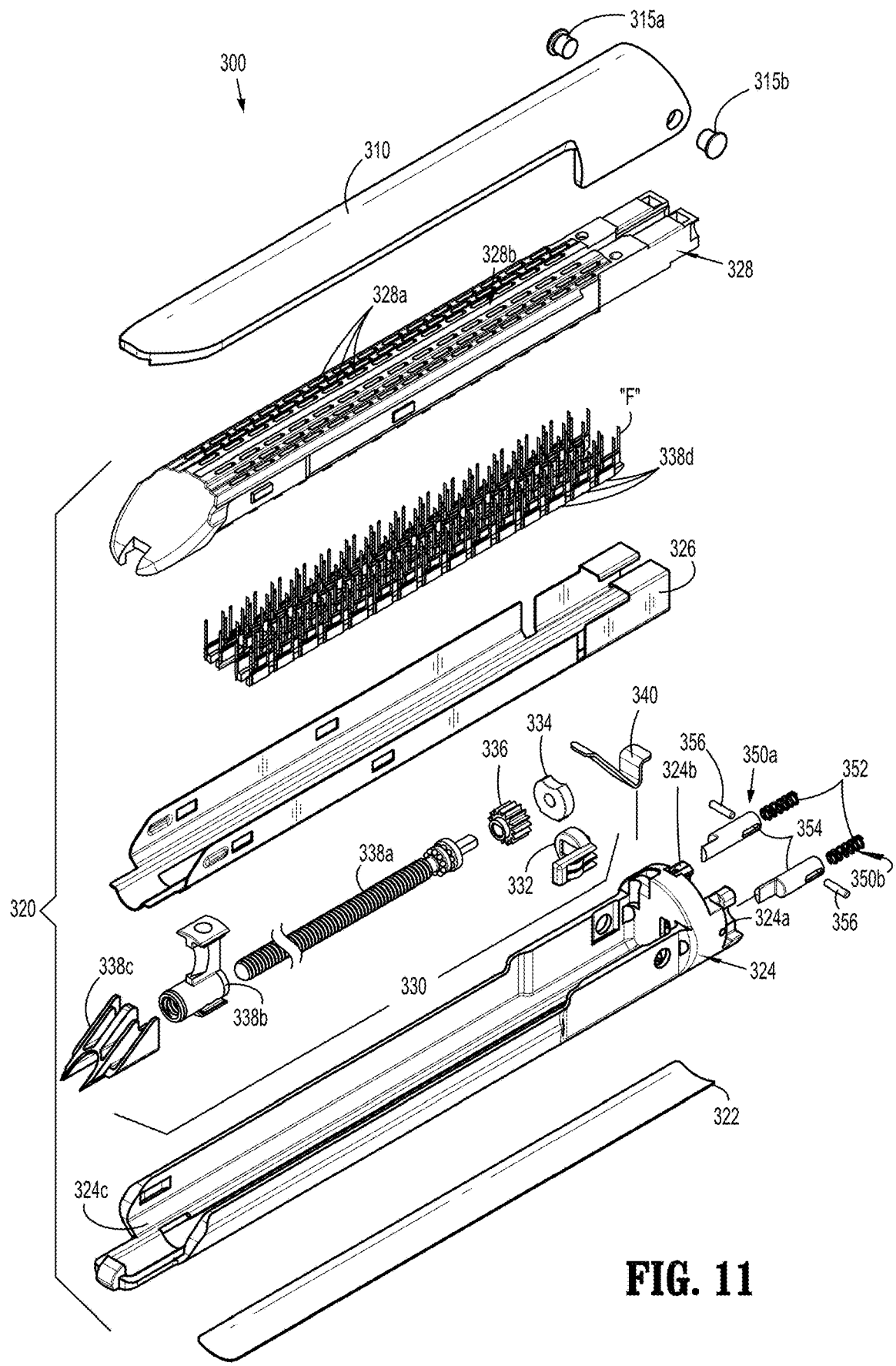
FIG. 11 is a perspective view, with parts separated, of an end effector of the electromechanical surgical system of FIG. 1.

Turning now to FIG. 11, an embodiment of an end effector 300 is shown. End effector 300 includes an anvil 310 and a cartridge assembly 320 that are pinned together by pins 315a, 315b and movable between open and closed conditions. Anvil 310 and cartridge assembly 320 cooperate to apply linear rows of fasteners "F" (e.g., staples). In certain embodiments, fasteners "F" are of various sizes, and, in certain embodiments, fasteners "F" are loaded into various lengths or rows of cartridge assembly 320 of end effector 300 (e.g., about 30, 45 and 60 mm in length).

Cartridge assembly 320 of end effector 300 includes a base 322 secured to a mounting portion 324, a frame portion 326, and a cartridge portion 328. Cartridge portion 328 has a tissue engaging surface that defines fastener retaining slots 328a and a knife slot 328b therein. Mounting portion 324 of cartridge assembly 320 has mating surfaces 324a, 324b on a proximal end thereof and defines a receiving channel 324c therein that supports frame portion 326, cartridge portion 328, and a fastener firing assembly 330 therein. Cartridge assembly 320 supports a biasing member 340 (e.g., a leaf spring) that engages anvil 310.

Fastener firing assembly 330 of end effector 300 includes an electrical contact member 332 for electrical communication with the circuit board of surgical device 100, a bearing member 334, a gear member 336 that engages rotatable gear 206a of adapter assembly 200, and a screw assembly 338. Screw assembly 338 of fastener firing assembly 330 includes a lead screw 338a, a drive beam 338b, and an actuation sled 338c that is engageable with pusher members 338d.

Cartridge assembly 320 of end effector 300 also supports plunger assemblies 350a, 350b. Each of plunger assemblies 350a, 350b includes a spring 352, a plunger 354, and a pin 356 that secures each plunger assembly to mounting portion 324 of cartridge assembly 320. Plunger assemblies 350a, 350b cooperate with the proximal end of cartridge portion 328 to facilitate securement of cartridge portion 328 within mounting portion 324.

In order to secure the proximal end of end effector 300 to distal end portion 206 of outer tube 204 of adapter assembly 200, the proximal end of end effector 300 is aligned with distal end portion 206 of adapter assembly 200 so that the proximal end of end effector 300 can be coupled to distal end portion 206 of adapter assembly 200 such that mating surfaces 324a and 324b of end effector 300 engage with distal end portion 206 of adapter assembly 200 and the teeth of gear member 336 of end effector 300 enmesh with the teeth of rotatable gear 206a of distal end portion 206 of adapter assembly 200.

In use, actuation pad 108 of surgical device 100 is actuated to rotate one or both of rotatable drive shafts 106a, 106c (e.g., clockwise and/or counterclockwise) of surgical device 100 via motors (not shown) disposed within surgical device 100.

Rotation of rotatable drive shaft 106a of surgical device 100 causes a corresponding rotation of worm gear 227d of worm drive assembly 227 and thus, rotation of lower gear 225a of gear assembly 225. Rotation of lower gear 225a of gear assembly 225 rotates lower capstan 225b of gear assembly 225 to draw/retract/tighten one side/end of cable 240a of cable drive assembly 220 while letting out/releasing the opposite side/end of cable 240a. Similarly, rotation of rotatable drive shaft 106c of surgical device 100 causes a corresponding rotation of worm gear 226d of worm drive assembly 226 and thus, rotation of upper gear 224a of gear assembly 226. Rotation of upper gear 224a of gear assembly 224 rotates upper capstan 224b of gear assembly 224 to draw/retract/tighten one side/end of cable 240b of cable drive assembly 220 while letting out/releasing the opposite side/end of cable 240b. Cables 240a, 240b of cable drive assembly 200 can be drawn/retracted/tightened and/or let out/released as desired to effectuate articulation (e.g., a pitch and/or a yaw) of end effector 300 about longitudinal axis "X" of adapter assembly 200.

To fire fasteners "F" from end effector 300, actuation pad 108 of surgical device 100 is actuated to rotate rotatable drive shaft 106b via a motor 103a (see FIG. 1) within handle housing 102, and to effectuate rotation of firing shaft 232 of firing assembly 230 about longitudinal axis "X" of adapter assembly 200. Rotation of firing shaft 232 of firing assembly 230 rotates rotatable gear 206a of distal end portion 206 of adapter assembly 200, which in turn, causes rotation of gear member 336 of end effector 300.

Rotation of gear member 336 of firing assembly 330 rotates lead screw 338a of firing assembly 330 and enables drive beam 338b of firing assembly 330 to axially advance along lead screw 338a and through longitudinal knife slot 328b of cartridge portion 328 by virtue of a threaded engagement between lead screw 338a and drive beam 338b. Drive beam 338b of firing assembly 330 engages anvil 310 of end effector 300 to maintain anvil 310 and cartridge assembly 320 of end effector 300 in approximation. Distal advancement of drive beam 338b of firing assembly 330 advances actuation sled 338c of firing assembly 330 into engagement with pusher members 338d of end effector 300 and fires the fasteners "F" from fastener retention slots 328a of cartridge portion 328 for forming against corresponding fastener forming pockets (not shown) defined within anvil 310. End effector 300 can be reset and cartridge portion 328 of cartridge assembly 320 can be replaced so that end effector 300 can then be re-fired as needed or desired.

Figure 12:
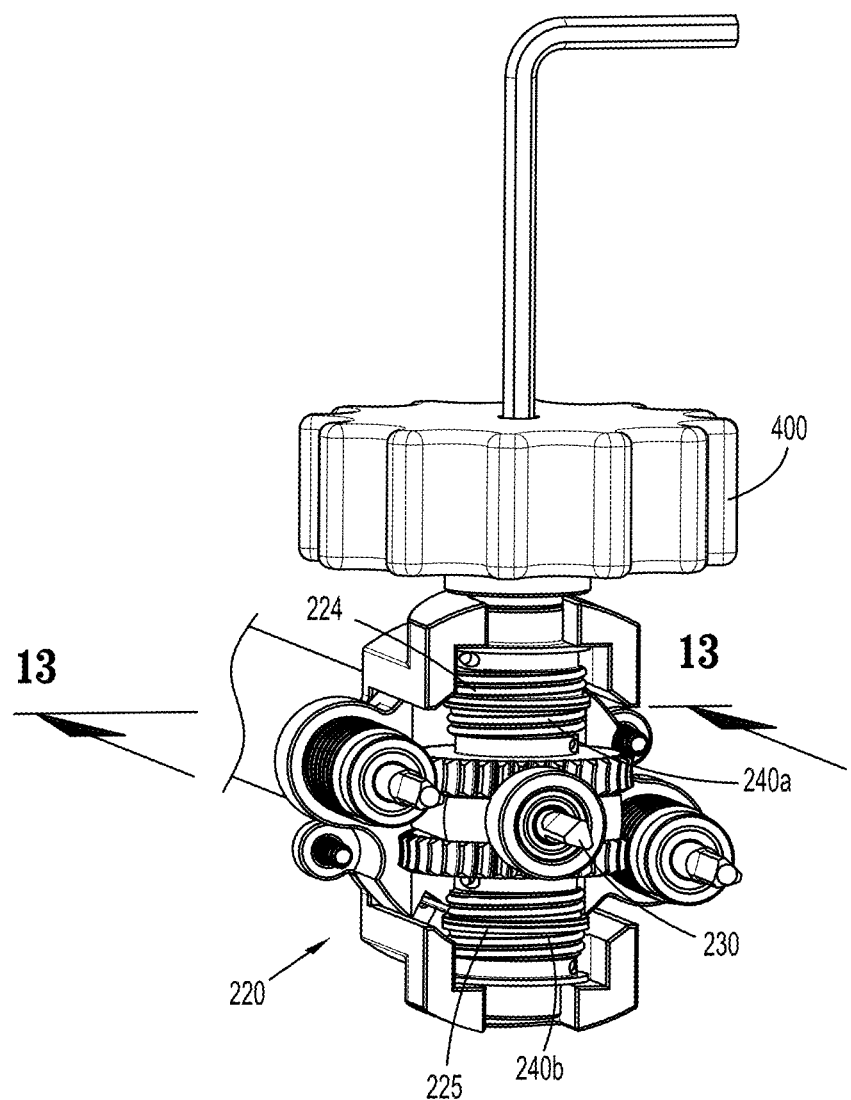
FIG. 12 is a perspective view illustrating cables of the drive system of FIG. 7 being tensioned with tensioning devices.

Turning now to FIGS. 12-14, upper capstan 224b of first cable gear assembly 224 defines a slot 224d therein and lower capstan 225b of second cable gear assembly 225 defines a slot 225d therein. Slots 224d, 225d of respective upper and lower capstans 224b, 225b are configured to selectively receive detents 402 of a rotatable knob 400 therein to enable tension in cables 240a, 240b to be adjusted upon rotation of upper and/or lower capstans 224b, 225b via rotation of rotatable knob 400. Rotatable knob 400 further defines a central channel 404 therethrough configured to selectively receive a fastener driver 500 (e.g., an Allen wrench) therethrough for tightening and/or loosening respective upper and lower fasteners 224c, 225c of respective first and second gear assemblies 224, 225 to further facilitate tension adjustments as needed or desired.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. An adapter assembly for selectively interconnecting an end effector to a handle assembly supporting a motor, the motor configured to impart drive force from the handle assembly to the end effector to operate the end effector, the adapter assembly comprising:
   a proximal housing body configured to couple to the handle assembly;
   a distal housing body coupled to the proximal housing body;
   an outer tube extending distally from the distal housing body and configured to support the end effector on a distal end portion of the outer tube; and
   a cable drive assembly supported between the proximal and distal housing bodies and including:
      a body portion having an upper portion and a lower portion;
      a first cable gear assembly supported on the upper portion of the body portion and supporting a first cable;

a second cable gear assembly supported on the lower portion of the body portion and supporting a second cable; and a plurality of guide pulleys supported between the body portion and the distal housing body, the plurality of guide pulleys configured to guide the first cable and the second cable through the distal housing body and into the outer tube for operating the end effector.

2. The adapter assembly of claim 1, wherein the body portion of the cable drive assembly defines proximal pulley recesses in a distal surface of the body portion, wherein a first set of the plurality of guide pulleys are supported in the proximal pulley recesses.

3. The adapter assembly of claim 2, wherein the distal housing body defines distal pulley recesses in a proximal surface of the distal housing body, wherein a second set of the plurality of guide pulleys are supported in the distal pulley recesses.

4. The adapter assembly of claim 3, wherein the outer tube defines a central longitudinal axis that extends from a proximal end portion of the outer tube to a distal end portion of the outer tube, wherein each guide pulley of the first set of the plurality of guide pulleys directs one of the first cable or the second cable in a direction transverse to the central longitudinal axis.

5. The adapter assembly of claim 4, wherein each guide pulley of the second set of the plurality of guide pulleys directs one of the first cable or the second cable in a longitudinal direction along the central longitudinal axis.

6. The adapter assembly of claim 5, wherein when portions of the first or second cable are disposed between the first and second sets of the plurality of guide pulleys, the portions are transverse to the longitudinal axis.

7. The adapter assembly of claim 6, wherein when the portions are disposed in a proximal position relative to the plurality of guide pulleys, the portions are parallel to the central longitudinal axis.

8. The adapter assembly of claim 7, wherein when the portions are disposed in a distal position relative to the plurality of guide pulleys, the portions are parallel to the central longitudinal axis.

9. The adapter assembly of claim 8, wherein in the distal position, the portions are closer to the central longitudinal axis than when the portions are disposed in the proximal position.

10. The adapter assembly of claim 4, wherein each of the first and second sets of the plurality of guide pulleys circumscribes the central longitudinal axis.

11. The adapter assembly of claim 10, wherein the first set of the plurality of guide pulleys is radially closer to the central longitudinal axis than the second set of the plurality of guide pulleys.

12. The adapter assembly of claim 1, wherein the cable drive assembly includes a first capstan that supports the first cable and a second capstan that supports the second cable.

13. The adapter assembly of claim 12, further comprising a first gear that rotates the first capstan and a second gear that rotates the second capstan.

14. The adapter assembly of claim 13, wherein at least one of the first or second gears is coupled to a worm gear.

15. The adapter assembly of claim 1, wherein the adapter assembly further includes a firing assembly that extends through the cable drive assembly and into the outer tube.

16. A surgical stapling apparatus, comprising:
an end effector;
a handle assembly configured to operate the end effector; and
an adapter assembly for selectively interconnecting the end effector and the handle assembly, the adapter assembly including:
a proximal housing body coupled to the handle assembly;
a distal housing body coupled to the proximal housing body;
an outer tube extending distally from the distal housing body and configured to support the end effector on a distal end portion of the outer tube; and
a cable drive assembly supported between the proximal and distal housing bodies and including:
a body portion having an upper portion and a lower portion;
a first cable gear assembly supported on the upper portion of the body portion and supporting a first cable;
a second cable gear assembly supported on the lower portion of the body portion and supporting a second cable; and
a plurality of guide pulleys configured to guide the first cable and the second cable through the distal housing body and into the outer tube for operating the end effector.

17. The surgical stapling apparatus of claim 16, wherein the cable drive assembly includes a first capstan that supports the first cable and a second capstan that supports the second cable.

18. The surgical stapling apparatus of claim 17, further comprising a first gear that rotates the first capstan and a second gear that rotates the second capstan.

19. The surgical stapling apparatus of claim 18, wherein at least one of the first or second gears is coupled to a worm gear.

20. An end effector assembly, comprising:
an end effector;
an adapter assembly for selective connection to the end effector and a handle assembly, the adapter assembly comprising:
a proximal housing body configured to couple to the handle assembly;
a distal housing body coupled to the proximal housing body;
an outer tube extending distally from the distal housing body and supporting the end effector on a distal end portion of the outer tube; and
a cable drive assembly supported between the proximal and distal housing bodies and including:
a body portion;
a first cable gear assembly coupled to the body portion and supporting a first cable;
a second cable gear assembly coupled to the body portion and supporting a second cable; and
a plurality of guide pulleys supported between the body portion and the distal housing body, the plurality of guide pulleys configured to guide the first cable and the second cable through the distal housing body and into the outer tube for operating the end effector.

* * * * *